United States Patent [19]

Goodman

[11] Patent Number: 5,547,380
[45] Date of Patent: Aug. 20, 1996

[54] METHOD OF USING ULTRASONIC DENTAL TOOL

[76] Inventor: Jack Goodman, 3011 Third St., North, Arlington, Va. 22201

[21] Appl. No.: 292,202

[22] Filed: Aug. 19, 1994

[51] Int. Cl.⁶ .................................................. A61C 3/03
[52] U.S. Cl. .......................................... 433/215; 433/119
[58] Field of Search ..................... 433/3, 18, 86, 433/118, 119, 150, 215, 218, 229

[56] References Cited

U.S. PATENT DOCUMENTS

| | | | |
|---|---|---|---|
| 4,127,125 | 11/1978 | Takemoto et al. | 433/86 |
| 4,725,233 | 2/1988 | Plunert | 433/150 |
| 4,772,202 | 9/1988 | Ebner Jr. | 433/150 |
| 5,106,302 | 4/1992 | Farzin-Nia et al. | 433/215 |
| 5,320,532 | 6/1994 | Farzin-Nia et al. | 433/215 |

*Primary Examiner*—Stephen Funk
*Assistant Examiner*—Steven S. Kelley
*Attorney, Agent, or Firm*—Eric P. Schellin

[57] ABSTRACT

Method and tool for fracturing the interface between dental structure that have been cemented together. The method is accomplished by positioning a rapid impacting tool at about 90° against the one side of the lower portion of a cap covering a tooth. The opposite side of the cap is abutted with a kinetic energy absorber. The flexing against the cap is small while the frequency is high.

3 Claims, 1 Drawing Sheet

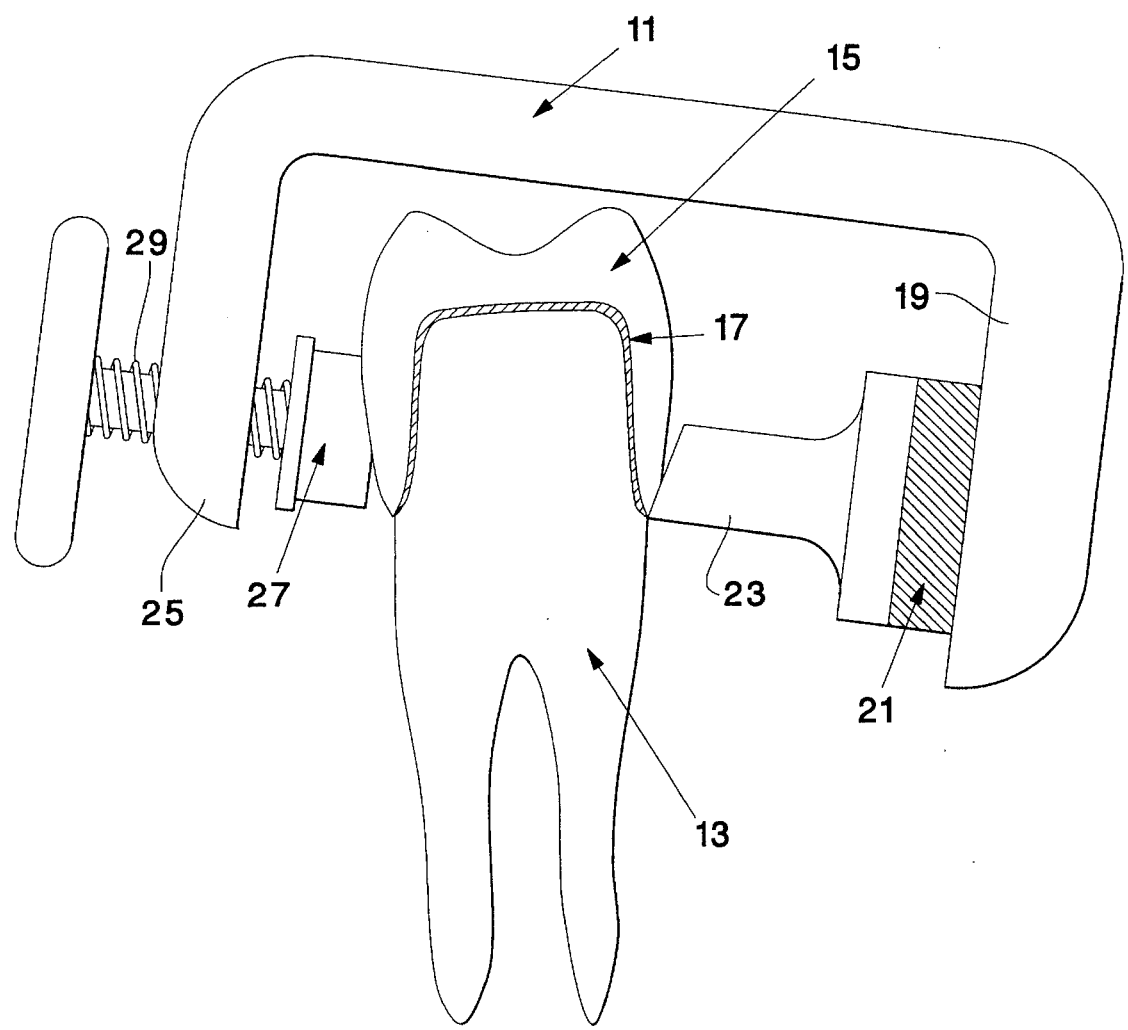

METHOD OF USING ULTRASONIC DENTAL TOOL

FIELD OF THE PRESENT INVENTION

The present invention relates to a dental tool and method of use, and more particularly, to a tool for fracturing the interface between two dental structures that have been secured together.

BACKGROUND OF THE PRESENT INVENTION

Dental structures such as caps, crowns and bridges are bonded to natural tooth roots by conventional cements. It is well known, that the removal of cemented dental structures may be necessary for one or more of the following reasons:

(a) The occurrence of dental decay.

(b) To examine the vitality and pulpal involvement of an underlying tooth.

(c) To repair cemented dental structures made defective by the wear of materials.

(d) The loss of selected supporting teeth.

It is also known that natural tooth roots are connected to bone structure by a matrix of connecting fibers. It is said that the connecting fibers exhibit a resultant vector force which holds the tooth root in place, which vector force operates substantially along a longitudinal axis in the direction of the top to bottom of the tooth. Thus, properly directed impacting forces permit the use of short force magnitude but of high frequency to break or fracture the cement bonds holding the dental structure to the tooth root with a minimal detrimental effect to the fibers or natural tooth roots.

In the prior art, removal of dental structures such as caps, crowns and bridges was achieved by sacrifice of the tooth, or, by application of a rigid grasping means to the structure followed by the manual application of an impacting or leverage force in an attempt to break the cement bonds. However, prior art devices could apply only in exact magnitudes of impacting forces since manual means were used. Such manual means were further limited in that the oral cavity is not large enough to permit easy direct impacting to those dental structures located near the rear of the cavity. Other consequences of the use of prior art apparatus are patient discomfiture, and in convenience to the dentist occasioned by the cumbersome mechanical apparatus.

Some recent progress has been made by the use of diminutive ultrasonic probes for working on teeth to remove orthodontics and other dental structures, such as disclosed in U.S. Pat. Nos. 5,106,302 and 5,320,532 to the Farzin-Nia et al

SUMMARY OF THE INVENTION

It is accordingly an object of this invention to provide a more efficient apparatus for the removal of a cemented dental structure.

It is another object of the invention to provide an apparatus for the removal of a cemented dental structure using precisely impacting forces directed transversely to the longitudinal axis of said structure.

It is still another object of this invention to provide an apparatus for the removal of a cemented dental structure operable in confined regions of the oral cavity.

It is an object of this invention to provide an automatic apparatus minimizing manual intervention for effecting the removal of a cemented dental structure.

It is another object of this invention to provide an apparatus for the removal of a cemented dental structure, which apparatus include a vise means to hold the dental structure.

It is still another object of this invention to provide an electrically operable ultrasonic apparatus for the removal of a cemented dental structure.

It is yet another object of this invention to provide an apparatus for the removal of a cemented dental structure, which apparatus may be selectively coupled to any one of a plurality of permanent cap, crown or bridge structures.

The direction of application of impacting must be applied perpendicular to the plane of the cement of the structure. In this way the cement bond is fractured by shocking it with many low power but high frequency shock waves. In use an ultrasonic tool or like high frequency impacting means is placed perpendicular to the axis of the tooth, at proximate the open end of the cap. The opposite side of the cap must be backed anvil-like by a absorbent or compliant material to reduce the possibility of placing any net strain on the root.

Preferably the compliant material and the ultrasonic tool is positioned at the confronting legs of a vise-like device whereby the cap of the tooth is positioned therebetween in gripping manner. The vise action results in maintaining constant contact of the tool with cap considerably inhibits the production of sound by the tool, thereby making it more pleasant for the patient. As said, the tool need not be operating in the ultrasonic range but may apply lower level impacts.

The concept is to flex the rim area of the cap very rapidly but with a minimum of lateral displacement, of the order of approximately five microns whereby the cement is trapped and fractured between the inertia of the root (or post) on the flexing cap. It has been discovered that the fracture line begins at the point of abutment of the ultrasonic tool and extends around the post or root to the other side of the cap. This greatly reduces the energy and time required to break the bond. There is no pulling forces on the root, only very small vibrations. Since there is no pulling or tugging on the root and the motion is small, large caps with multiple posts or roots work extremely well by fracturing the cement at each bond individually.

DESCRIPTION OF THE DRAWINGS

The FIGURE is a perspective of clamp having the ultrasonic tool or impact tool on one leg and a compliant surface on the opposite leg with a capped tooth in cross-section positioned therebetween.

DETAILED DESCRIPTION OF THE PREFERRED EMBODIMENT

Referring to the FIGURE there is shown a vise or clamp 11 which has two opposed legs which is detailed to be mounted on a tooth 13 having a conventional cap 15 which is to be removed. The cap 15 has underlying cement 17 by means of which the cap is adhered to the tooth 13.

The clamp 11 has disposed on one leg 19, an ultrasonic tool 21 positioned whereby its horn 23 is positioned perpendicular to the tooth 13. The other leg 25 has an abutment 27 which is driven by a screw 29. The abutment 27 is of compliant material having some resiliency but basically is designed to limit the movement of the cap portion of the tooth to the degree of flexing imposed by the ultrasonic tool or like tool 23, i.e. about 5 microns.

Once the fracturing has been completed the clamp 11 can be removed, followed by the removal of the cap 15. In the event the fracturing is incomplete the clamp 11 may be re-positioned for further impact impingement. At no time with the method of the invention is it necessary to apply pulling forces on the cap or tooth which can result in loosening of the tooth per se.

It is to be understood that various other changes and modifications may be made without departing from the scope of the present invention. The present invention being only limited by the claims.

What is claimed is:

1. A method for disintegrating the cement which adheres a cap to a tooth thereby loosening the cap for removable comprising the steps of:

providing an adjustable clamp, wherein said clamp has two legs, one leg having an ultrasonic device mounted thereon adapted and constructed to lie in abutment of a lower portion of said cap on one side thereof, said other leg having a compliant means adapted and constructed to lie in abutment of a lower portion of said cap on the other side thereof, clamping said device on the lower portion of opposite sides of a cap mounted on a tooth whereby the ultrasonic device is substantially perpendicularly held against one side of said lower portion of said cap, maintaining in abutment said compliant means against the opposite side of a lower portion of said cap thereby inhibiting lateral movement of said cap, activating said ultrasonic device to impinge lateral strokes against the side of said cap against which the ultrasonic device abuts controlling the lateral strokes of the ultrasonic device whereby lateral motion imparted to the said side of said cap is less than 10 microns, whereby causing a disintegrating of the cement to occur at said side of said lower portion of said cap to which the ultrasonic device impinges, permitting the said disintegrating to extend around to the other side of the said cap while continuing the activation of the ultrasonic device until the said cap is completely loosened, thereafter removing said cap.

2. The method of claim 1 wherein the device is an ultrasonic tool.

3. The method of claim 2 wherein the vibrations of the ultrasonic tool is at 20 KHZ and the deflection movement is about 5 microns.

* * * * *